(12) United States Patent
Pickbrenner et al.

(10) Patent No.: US 10,494,650 B2
(45) Date of Patent: Dec. 3, 2019

(54) PROCESS FOR PRODUCTION OF BIOGAS

(71) Applicant: Rheinkalk GmbH, Wülfrath (DE)

(72) Inventors: Arnd Pickbrenner, Wülfrath (DE);
Heiko Saure, Gevelsberg (DE);
Christopher Pust, Düsseldorf (DE);
Volker Spicker, Wülfrath (DE)

(73) Assignee: Rheinkalk GmbH, Wülfrath (DE)

( * ) Notice: Subject to any disclaimer, the term of this patent is extended or adjusted under 35 U.S.C. 154(b) by 819 days.

(21) Appl. No.: 14/347,771

(22) PCT Filed: Sep. 21, 2012

(86) PCT No.: PCT/EP2012/068669
§ 371 (c)(1),
(2) Date: Feb. 12, 2015

(87) PCT Pub. No.: WO2013/045368
PCT Pub. Date: Apr. 4, 2013

(65) Prior Publication Data
US 2016/0194666 A1 Jul. 7, 2016

(30) Foreign Application Priority Data

Sep. 28, 2011 (DE) .................. 10 2011 114 441
Mar. 22, 2012 (DE) .................. 10 2012 005 636

(51) Int. Cl.
*C12P 5/02* (2006.01)
*C10L 3/08* (2006.01)
*C02F 11/04* (2006.01)

(52) U.S. Cl.
CPC .............. *C12P 5/023* (2013.01); *C10L 3/08* (2013.01); *C02F 11/04* (2013.01); *C10L 2200/0469* (2013.01); *C10L 2290/26* (2013.01); *Y02E 50/343* (2013.01); *Y02W 10/37* (2015.05)

(58) Field of Classification Search
None
See application file for complete search history.

(56) References Cited

U.S. PATENT DOCUMENTS 8,092,680 B2   1/2012   Johnson

FOREIGN PATENT DOCUMENTS

| DE | 100 34 279 | 2/2002 |
|---|---|---|
| DE | 10 2007 043 751 | 3/2009 |
| EP | 0 218 896 | 4/1987 |
| EP | 2 090 660 | 8/2009 |
| FR | 2 924 441 | 6/2009 |
| JP | H0632708 | 2/1994 |

OTHER PUBLICATIONS

SIDS Initial Assessment Report for SIAM 15,Sodium bicarbonate, retrieved from the internet, Mar. 28, 2017: http://www.inchem.org/documents/sids/sids/sodbicarb.pdf.*
HMK Product Information Particle Size Distribution D50, retrieved from the Internet, Oct. 4, 2017: www.hmk-test.com/particle-size-distribution-d50/.*
HMK Product Information What is D97 , retrieved from the Internet, Oct. 4, 2017: www.hmk-test.com/what-is-d97what-is-the-purpose-of-it/.*
Bishop et al., Particle Size and Plasticity of Lime, Journal of Research of the National Bureau of Standards, vol. 23, Aug. 1939, pp. 285-292.*
Huang et al., Limestone Particle Size and Residual Lime Concentration Affect pH Buffering in Container Substrates, Environmental Horticulture Dept., University of Florida, Journal of Plant Nutrition, vol. 33, Issue 6, 2010, published online Apr. 5, 2010; retrieved from the internet: https://hort.ifas.ufl.edu/.*
German Office Action dated Jun. 12, 2017 (in German), 8 pages.
Stokessche Gleichung, retrieved from the Internet Apr. 16, 2012, http://de.wikipedia.org/wikl/Stokessche_Gleichung.
Pufferkapazität, retrieved from the Internet, Apr. 16, 2012, http://de.wikipedia.org/wiki/Pufferkapazit%C3%A4t.

* cited by examiner

*Primary Examiner* — Thomas J. Visone
*Assistant Examiner* — Evelyn Y Pyla
(74) *Attorney, Agent, or Firm* — Honigman LLP; Thomas A. Wootton, Esq.; Jonathan P. O'Brien

(57) ABSTRACT

The invention relates to a process for production of biogas from a biodegradable substrate under anaerobic conditions, comprising the steps of introducing the substrate into a reaction space, the addition of a lime-based material having a particle diameter ($d_{97}$) of less than 90 μm and/or ($d_{50}$) of less than 10 μm to the substrate, and the biodegradation of the substrate to form biogas.

24 Claims, 9 Drawing Sheets

PROCESS FOR PRODUCTION OF BIOGAS

CROSS-REFERENCE TO RELATED APPLICATIONS

This application claims priority under 35 U.S.C. 371 to Patent Cooperation Treaty application PCT/EP2012/068669, filed Sep. 21, 2012, which claims the benefit of earlier filed German Application 102012005636.2, filed Mar. 3, 22, 2012, and from earlier filed German Application 102011114441.6, filed Sep. 28, 2011, the entire contents of which are incorporated herein by reference.

TECHNICAL FIELD OF THE INVENTION

The invention relates to a process for production of biogas from a biodegradable substrate under anaerobic conditions as well as biogas produced using this process. The invention also relates to the use of lime-based materials to stabilise the process according to the invention.

BACKGROUND OF THE INVENTION

The increasing scarcity of raw materials for energy production has created a growing need worldwide to produce energy from renewable resources. Due to its continuous availability, regardless of short-term fluctuations in wind or sunlight, bioenergy, and thus also biogas, makes a worthwhile contribution as an addition to the energy mix of renewable energy sources.

The production of thermally useable gas mixtures from biodegradable substrates (biogas extraction) represents a technically relatively easy process for converting biomass into energy. The biochemical decomposition of organic substances by microorganisms under anaerobic conditions (fermentation) is well known.

Prior to processing, biogas itself is a mostly water-saturated combustible gas mixture comprising the main components methane ($CH_4$) and carbon dioxide ($CO_2$). It also contains small quantities of nitrogen ($N_2$), oxygen ($O_2$), hydrogen sulphide ($H_2S$), hydrogen ($H_2$) and ammonia ($NH_3$). The methane content is the most important in terms of the utilization of biogas since, as said methane is an oxidisable compound, it releases energy during combustion.

To increase the economic efficiency of biogas production, general efforts are made to convert the biomass used as fully as possible. Maximising the volumetric loading (mass of dry organic substance added per unit of fermenter volume and time) is also desirable. At the same time, substrates that are as energy-rich as possible are used.

However, volumetric loadings that are too high can also easily lead to an imbalance in the multi-stage fermentation process. Acidification in the fermenter caused by this leads to the inhibition of methanogenic microorganisms. In extreme cases, this can lead to a complete disruption of the process. In order to offset acidification processes of this kind, it is customary to reduce the substrate supply where required. If this course of action is unsuccessful, a complete replacement of the reactor content is required. The subsequent starting of the fermentation process until maximum gas yield has been achieved can take up to twelve weeks. The reduction in methane production or the complete disruption with subsequent start-up results directly in reduced profits.

Another common method for process stabilisation consists in countering substrate acidification by adding neutralising additives. Lime-based products have proven particularly suitable for this purpose. JP 632708 describes the anaerobic fermentative treatment of a mixture of liquid soya bean residue and aluminium oxide, wherein a combination of zeolites and burnt lime (CaO) is added to enhance fermentation.

The use of lime-based products to stabilise biogas production is also known from DE 100 34 279 A1. This document describes a process for controlling a biogas plant in which parameters of the silage effluent, for example, pH value, which are important in terms of methanation, are measured using a measuring device. It discloses that hydrated lime or lime milk is added if the pH falls below a specific value, and consequently the pH value rises to the required level again. EP 2 090 660 A1 describes a method for producing biogas by adding carbonated lime.

The disadvantage of the known methods is that the lime-based products added tend to settle in the bioreactor which leads to a reduction in their effectiveness.

SUMMARY OF THE INVENTION

The object on which the invention is based consists in providing a process of the type referred at the start with which the pH value of the biodegradable substrate can be stabilised reliably using lime-based products, during biodegradation. Thus, the addition of lime-based products is intended to lead to maintenance of the required buffer capacity of the fermenter content. In particular, the process according to the invention is intended to ensure that the stabilising effect of the lime-based products can be exploited in the best possible manner.

This object is achieved according to the invention by a process for production of biogas from a biodegradable substrate under substantially anaerobic conditions, comprising the steps of introducing the substrate into a reaction space, adding a lime-based material having a particle diameter $d_{97}$ of less than 90 μm and/or a particle diameter $d_{50}$ of less than 10 μm, and the biodegradation of the substrate under formation of biogas.

DETAILED DESCRIPTION OF THE INVENTION

The process according to the invention is characterised in that fine-particle, lime-based materials are used as an additive to stabilise the fermentation process when producing biogas. It was discovered surprisingly that additives of this kind show no or only a slight tendency to settle in the fermenter. Thus, in the process according to the invention, the pH value can be stabilised reliably during the fermentation process. This enables the use of high-energy substrates at a simultaneously high volumetric loading.

The use of lime-based materials in the process according to the invention is also characterised in the fact that it enables production of biogas with a high methane content. Moreover, lime-based materials generally have the advantage of hygienically purifying the organic substances used as substrate. This is particularly advantageous when using agricultural waste.

The most varied substances can be used as lime-based material in the process according to the invention. Practical tests have shown that particularly good results are achieved with hydrated lime, lime milk, lime stone powder, caustic lime, dolomite stone powder, semi-burnt dolomite, dolomite hydrate, semi-hydrated dolomite and/or sodium hydrogen carbonate.

According to the invention, the lime-based material has an average particle diameter $d_{97}$ of less than 90 μm, more particularly between 1 and 70 μm. It was found that adjusting the particle diameter $d_{97}$ to values below 90 μm is enough to prevent sedimentation in the bioreactor to an adequate extent.

Particularly good results are achieved with lime-based materials, which have a particle diameter $d_{97}$ from 1 to 50 μm, preferably from 8 to 40 μm, more preferably from 6 to 30 μm, in particular from 4 to 15 μm, and/or a particle diameter $d_{50}$ from 0.1 to 10 μm, preferably from 1 to 8 μm.

Good results are also achieved with lime-based materials having a particle diameter $d_{97}$ of less than 50 μm, preferably less than 25 μm and in particular less than 15 μm.

The pH value of the substrate used can be stabilised reliably during biodegradation in the process according to the invention by adding the additives. Thus, acidification of the substrate can be countered effectively, for example, if the volumetric loading is increased and/or the energy density of the substrate used is high.

The target pH value in a plant depends on the plant type, the plant and process parameters as well as the substrates and microbial cultures used and can be determined by a person skilled in the art through tests. It has been shown that the best results are generally achieved at pH values of between 6.5 and 7.5.

According to a preferred embodiment of the invention, the addition of lime-based material takes place in accordance with requirements in order to counter an impending acidification of the substrate. In said embodiment, the lime-based material is added advantageously if the pH value of the substrate falls below 7.5, preferably below 7.0.

Particularly good results are achieved if the lime-based material is added when the measured pH value of the substrate deviates from the respective target pH value for the substrate by a maximum of 0.5, preferably a maximum of 0.2.

On the other hand, it may be advantageous in other cases to add the lime-based material as a preventative measure to stabilise the biological substrate. Such an approach, where the lime-based material can be added irrespective of the pH value of the substrate, is particularly advantageous if continuous monitoring of the process parameters in the bioreactor is to be avoided. Advantage is taken in this process alternative of the fact that adding the lime-based material increases the buffer capacity of the substrate thus preventing acidification.

If the lime-based material is used as a preventative measure, it is advisable to add it at the start of biogas production. In this way, acidification of the substrate can be prevented effectively throughout the entire fermentation process.

The quantity of lime-based material added can vary considerably according to the invention. It is advisable to adjust the quantity added depending on the energy density of the biodegradable substrate used as well as in consideration of the respective volumetric loading in the bioreactor. Practical tests have shown that it is useful in most cases to add the lime-based material at a quantity of from 0.0001 to 0.05 mol/l, preferably from 0.001 to 0.02 mol/l, and in particular from 0.005 to 0.01 mol/l, based respectively on the total volume of fermenter content.

If the addition of lime-based material is intended to counter imminent or existing acidification in the bioreactor, the lime-based material is added preferably at a quantity such that the pH value of the substrate is adjusted to from 6 to 8, preferably from 6.3 to 7.8, and in particular from 6.8 to 7.5. It should be noted when adopting this approach that adjustment of the pH value in the substrate depending on the lime-based material used, its particle size as well as the intermixing in the bioreactor can take varying periods of time. Practical tests have shown that the pH value regulating effect of semi-burnt dolomite is delayed. Such delayed effect is advantageous, since due to the size of the fermenter and the low specific energy input of the stirrers, mixing periods are generally very long. The delayed effect of semi-burnt dolomite therefore allows good distribution prior to the initiation of the pH value regulating effect. This leads to particularly good utilisation of the stabilising effect of semi-burnt dolomite.

If the lime-based material is intended as a preventative measure to increase the buffer capacity of the substrate, the lime-based material is added preferably at such quantity that the buffer capacity, expressed as $CaCO_3$ concentration per litre of reaction space, is adjusted to a value greater than 5 g/l, preferably greater than 10 g/l, more preferably greater than 15 g/l and in particular from 15 to 20 g/l.

The biodegradation of substrates in the process according to the invention can take place in a known manner. Biodegradation will generally include the following steps:

splitting of carbohydrates, fats and/or proteins in the substrate into cleavage products comprising sugar, fatty acids, amino acids and/or bases;

fermentation of the cleavage products into fermentation products comprising carboxylic acids, gases and/or alcohols;

formation of methanogenic substrates comprising acetic acid, hydrogen and/or carbon dioxide;

formation of biogas comprising methane and carbon dioxide.

The splitting of carbohydrates, fats and/or proteins contained in the substrate by hydrolytic bacteria, the fermentation of the cleavage products into fermentation products by fermentative bacteria, the formation of methanogenic substrates by acetogenic bacteria and the formation of biogas by methanogenic bacteria can take place within this reaction scheme.

Since the bacteria of the individual decomposition stages impose different requirements on their living environment, it may be advisable according to the invention for biodegradation to take place in a multi-stage system. In this way, particularly good account can be taken of the needs of the bacteria of the individual decomposition stages and a particularly high biogas yield achieved.

However, it is possible according to the invention to allow the individual stages of biodegradation to take place in the same reaction space. Thus, it is preferred according to the invention to allow at least two, preferably three, more preferably all four stages of biodegradation to take place in the same reaction space. Such management of the reaction has the advantage that particularly minimal technical complexity is required. Moreover, it is advantageous in this process alternative to find a compromise with regard to the environment required by the individual bacteria. The pH value in the reaction space is particularly relevant.

It was found in this context that methane bacteria respond most sensitively to process disruptions and at the same time are the slowest to increase in number. For this reason, it is preferred according to the invention to adjust the environment in the bioreactor in accordance with the requirements of said microorganisms. Adjusting the pH value of the substrate in the bioreactor to from 6.8 to 7.5 has proved useful for this purpose. Such a pH value is also advantageous in respect of the activity of acetogenic bacteria.

Moreover, in order to guarantee as much activity as possible, in particular of methane bacteria, it has proven advantageous if a biodegradable substrate with a C:N:P:S ratio of approx. 600:15:5:1 is used. Good results are also achieved with a biodegradable substrate with a C:N ratio of from 10 to 30. Furthermore, using a substrate with a concentration of inhibitors that is as low as possible is also advantageous for the decomposition process.

The adjustment of the reaction temperature in the fermenter to from 28° C. to 58° C., preferably from 32° C. to 42° C., particularly in biogas plants operated under mesophilic conditions, has also proven advantageous in terms of bacterial activity.

A further important parameter for the process according to the invention is the volumetric loading of the bioreactor. Volumetric loading is understood according to the invention as the mass of organic dry substance of the substrate used added per unit of fermenter volume and time. The volumetric loading of the bioreactor can fluctuate widely in the process according to the invention. It is advantageous to adjust the volumetric loading taking account of the plant technology used, the energy density of the substrate employed and the type and quantity of the lime-based material used.

Practical tests have shown that good results can generally be achieved with volumetric loadings of from 0.5 to 5 kg ods/m$^3$ per day, preferably 1 to 3 kg ods/m$^3$ per day. It is advisable to select as high a volumetric loading as possible in order to achieve a high gas yield and thus run the process according to the invention economically.

The lime-based material is advantageously added at a quantity of from 0.0001 to 0.05 mol/l, preferably from 0.001 to 0.02 mol/l, and in particular from 0.005 to 0.01 mol/l, based respectively on the total volume of fermenter content.

The process according to the invention can be carried out in a conventional bioreactor, often referred to as a fermenter. A differentiation is generally made between bioreactors based on their design and function. Any bioreactor can handle three phases: solid (biomass), liquid (nutrient solution) and gaseous (for example, air, oxygen, carbon dioxide, nitrogen, methane).

The selection of the respective suitable bioreactor depends advantageously on the requirements in regard to the biological process. An effective stirrer speed with a high number of revolutions, for example, increases the homogeneity of the medium in the reactor and the oxygen input. Too vigorous stirring should preferably be prevented in bioreactors in order to preserve the bacterial community.

A differentiation is made between the following depending on the nature of filling:
batch processes, in which the reactor is filled to maximum and then emptied completely again at the end of a specific time interval ('reaction time' or 'growth time').
fed-batch processes, in which the fill level is below the maximum capacity of the reactor at the start and is then slowly increased up to maximum capacity using nutrient solution. The reactor is then emptied completely again.
continuous processes, in which a constant supply of nutrient solution and an equally large flow of 'sludge' (mixture of nutrient solution, product, biomass etc.) keep the fill level constant.

In order to achieve optimum product yield, it can be advisable to monitor the conditions inside the apparatus with the help of sensors. The pH value, oxygen, carbon dioxide content in the waste air, temperature and foam development can thus be measured by means of test probes.

Furthermore, constant monitoring of the quantity of biogas and its composition (methane, $CO_2$, $O_2$, $SO_2$ content) preferably takes place.

The most varied substances can be used according to the invention as biodegradable substrate. The following starting materials are suitable for the technical production of biogas:
fermentable, residual materials containing biomass, such as effluent sludge, biological waste or food waste
farm fertilisers (slurry, dung)
unused plants or plant parts (for example, catch crops, grass-clover in organic farming)
specifically cultivated energy crops (renewable raw materials).

Agriculture with the last three options represents the greatest potential for biogas production. With the exception of the last option, these starting materials cost nothing in principle (apart from transport and other incidental costs). Particularly suitable substrates according to the invention are renewable raw materials. The also extremely important requirement for trace elements can be covered for the most part by using slurry and dung.

Another object of the invention is the use of a lime-based material with a particle diameter $d_{97}$ of less than 90 μm, preferably from 1 to 70 μm, more preferably from 1 to 50 μm, even more preferably from 8 to 40 μm, more preferably again from 6 to 30 μm, and in particular from 4 to 15 μm, as an additive to adjust the pH value of a biodegradable substrate when producing biogas. Alternatively, a lime-based material with a particle diameter $d_{50}$ of less than 10 μm can also be used.

The lime-based material is used preferably according to the invention to adjust the pH to a value from 6.3 to 8.0, preferably from 6.8 to 7.5.

Using the lime-based material to increase the buffer capacity of the organic substrate is also preferred.

It is advantageous to increase the buffer capacity, expressed as $CaCO_3$ concentration per litre of reaction space, to a value greater than 10 g/l, preferably greater than 15 g/l and in particular from 15 to 20 g/l.

According to a further preferred embodiment of the invention, the lime-based material is used as an additive to produce biogas with a higher methane content. Thus, the biogas according to the invention can have a methane content greater than 68% by volume, preferably from 50 to 75% by volume of methane, preferably from 60 to 75% by volume of methane and in particular from 65 to 70% by volume of methane.

The biogas produced using the process according to the invention is extremely well suited after appropriate processing for use in cogeneration plants, more particularly in combined heating and power stations. Since processing to natural gas quality is advisable, it is advantageous for this purpose to remove the $CO_2$ as far as possible. The so-called biomethane or bio natural gas obtained in the process can be compressed to 200 to 300 bar so that it can then be used in appropriate motor vehicles.

BRIEF DESCRIPTION OF THE DRAWINGS

The invention is described in greater detail below using figures that merely represent example embodiments in which.

The following lime-based materials are used as additives in the following embodiments:
1. Biocal H (=LH, lime hydrate, $Ca(OH)_2$)
   calcitic
   fine particle size ($d_{50}$=7 μm, $d_{97}$<60 μm)
2. Biocal C (=LSP, lime stone powder, $CaCO_3$)
   calcitic
   fine particle size ($d_{50}$=9 μm, $d_{97}$<70 μm)
3. Biocal CM (=SB, semi-burnt, $CaCO_3*MgO$)
   dolomitic
   fine particle size* ($d_{50}$=10 μm, $d_{97}$<90 μm)
   activation by neutralising the magnesium content (semi-burnt)
4. Bicar (sodium hydrogen carbonate, $NaHCO_3$)
5. Biocal SL (=lime milk, $Ca(OH)_2$)
   calcitic
   fine particle size ($d_{50}$=2.5 μm, $d_{97}$=10 μm)
6. Biocal HM (=dolomitic lime hydrate)
   dolomitic
   fine particle size ($d_{50}$=8 μm, $d_{97}$=50 μm)

1. Batch Fermentation Tests

The effectiveness of adding fine-particle, lime-based materials is analysed in batch fermentation tests during the fermentation of organic substrates where the substrate is added once.

The batch tests are conducted as follows:

Slurry is used as the substrate. The substrate is acidified to a pH value of approximately 6.3 using crushed grain. Maize silage as well as the additive under analysis is then added. Fermentation subsequently takes place over a period of 35 days.

The additive can be metered based on substance quantity or on pH value. Metering based on substance quantity is understood in the following examples as the same quantity of active ions being added in each case (for example, 0.012 mol/l of Biocal H, 0.024 mol/l of Biocal C). Metering based on pH value is understood as being the addition of the respective additive until a pH value of 7.5 is reached. Here, the different dissolving kinetics can lead to a different consumption from the case of metering based on substance quantity. In metering based on pH value, the respective additive is added in each case when the pH value falls below 7.5.

At the end of the test period of 35 days, the following parameters are analysed:
  pH value
  buffer capacity
  biogas production
  methane gas production.

Figure 1:
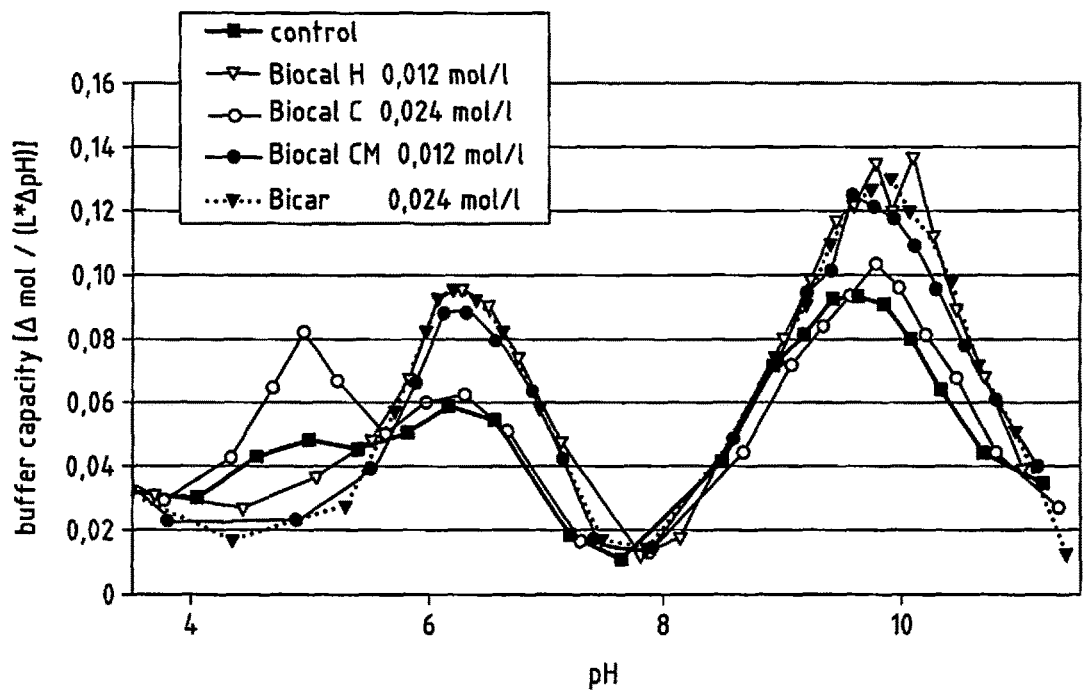
FIG. 1 shows the buffer capacity in a batch fermentation test where additive metering is based on substance quantity.

1.1 Determination of Buffer Capacity After 35 Days Fermentation in the Case of Additive Metering Based on Substance Quantity FIG. 1 shows the buffer capacity of the substrate as a function of pH value in the case of additive metering based on substance quantity in relation to Biocal H. As can be seen from FIG. 1, adding the additive leads to increased buffer capacity in all cases. Moreover, it shows that the effect of Biocal H and Biocal CM as well as Bicar is most pronounced at a pH value of 6.5.

Figure 2:
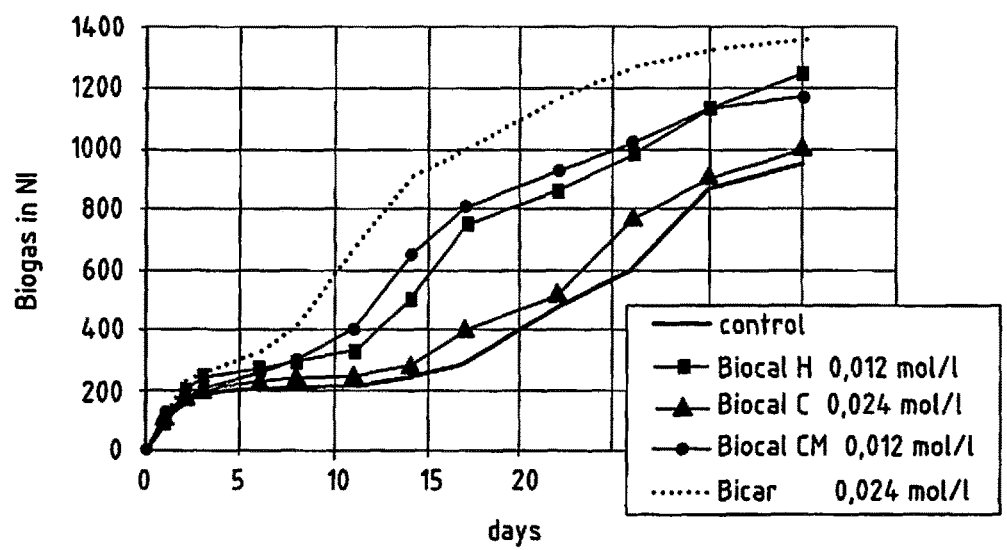
FIG. 2 shows biogas production in a batch fermentation test where additive metering is based on substance quantity.

1.2 Determination of Biogas Production After 35 Days Fermentation in the Case of Additive Metering Based on Substance Quantity FIG. 2 shows biogas production in the case of additive metering based on substance quantity in relation to Biocal H. It is evident from the graph that at the end of a test period of 35 days, the total volume of biogas is greater when using the lime-based materials employed.

1.3 Determination of Methane Gas Production After 35 Days Fermentation (Additive Metering Based on Substance Quantity)

Figure 3:
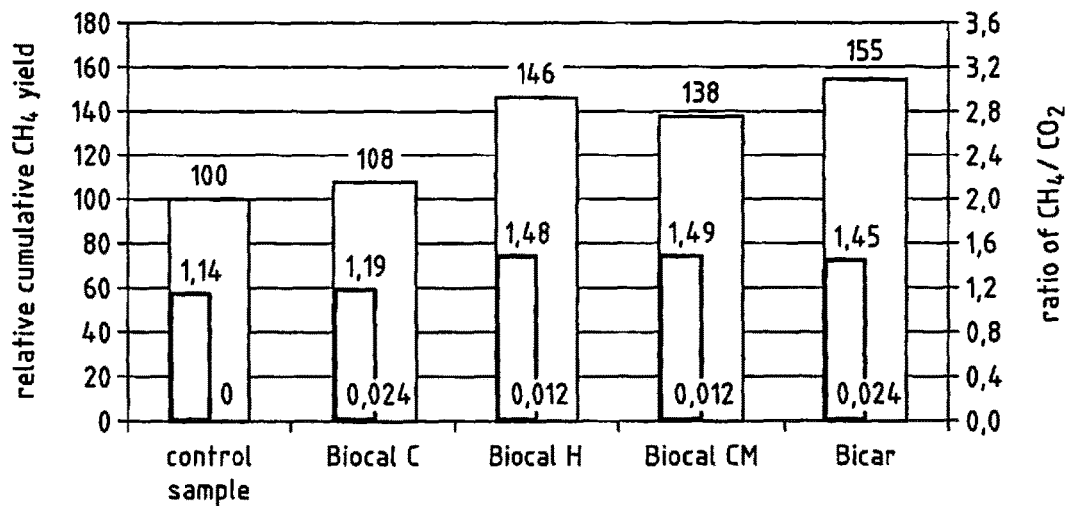
FIG. 3 shows methane gas production in a batch fermentation test where additive metering is based on substance quantity.

FIG. 3 shows methane gas production after 35 days in the case of additive metering based on substance quantity in relation to Biocal H. It is evident from FIG. 3 that the methane content in the biogas increases when the lime-based materials are used. Furthermore, it shows that the ratio of methane to carbon dioxide in the biogas is increased most by using Biocal CM.

1.4 Determination of Biogas Production After 35 Days Fermentation (Additive Metering Based on pH Value)

Figure 4:
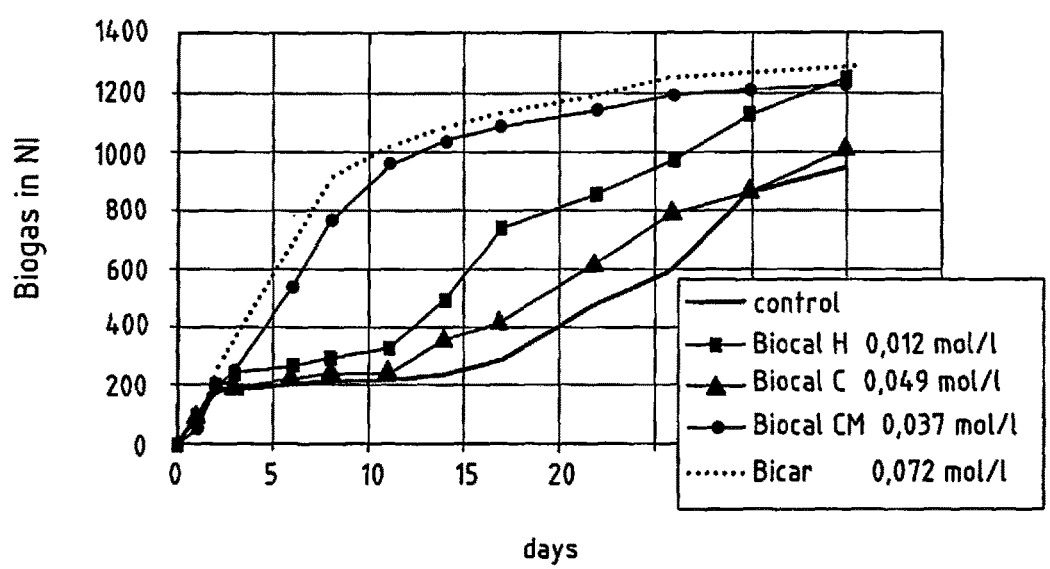
FIG. 4 shows biogas production in a batch fermentation test where additive metering is based on the pH value.

FIG. 4 shows biogas production after 35 days in the case of additive metering based on pH value (max. pH=7.5). It is evident from FIG. 4 that the total volume of biogas increases when using the lime-based materials.

1.5 Determination of Methane Gas Production After 35 Days Fermentation (Additive Metering Based on pH Value)

Figure 5:
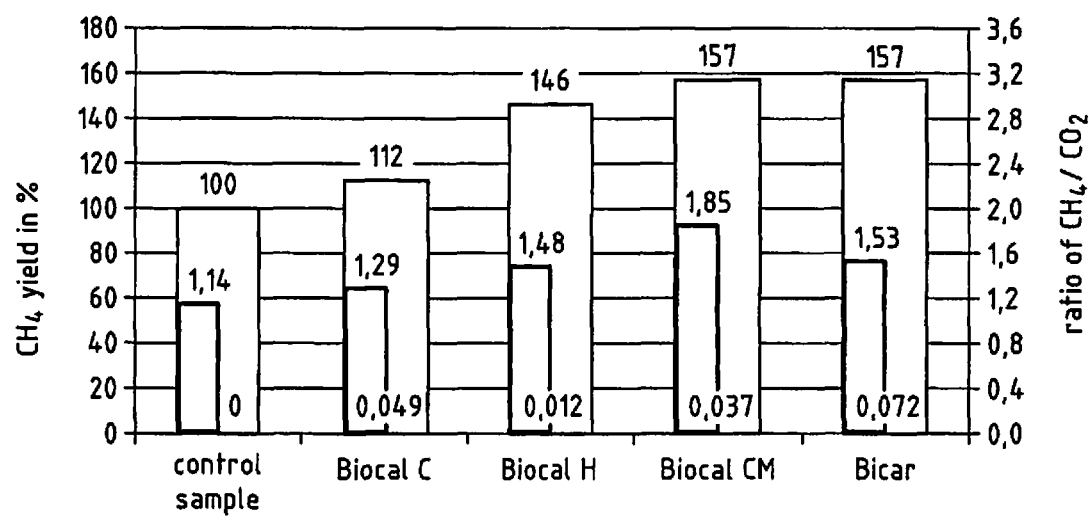
FIG. 5 shows methane gas production in a batch fermentation test where additive metering is based on the pH value.

FIG. 5 shows methane gas production after 35 days in the case of additive metering based on pH value (max. pH=7.5). The quantity of Biocal C, Biocal CM and Bicar added is increased in this test compared with the test shown in FIG. 3. It is clear from FIG. 5 that methane gas production can be increased further if larger quantities of additive are metered.

1.6 Summary Assessment of Batch Tests
  The buffer capacity of fermenter content charged with the additives is higher than the buffer capacity of unmodified fermenter content.
  At the end of a test period of 35 days, the total volume of biogas and, in particular methane gas, is higher when the additives are used.
  The addition of additives based on pH value can maximise the biogas yield after the shortest period of time (faster process regeneration).
  It should be emphasised that the methane/carbon dioxide ratio is best, particularly when using Biocal CM in a pH value based approach (see FIGS. 3/5).

2. Continuous Tests

In these fermentation tests, the effectiveness of adding fine-particle, lime-based materials is analysed during the fermentation of organic substrates where the process is managed continuously.

The continuous tests are carried out as follows:

Slurry is used as the base substrate. It is fed daily with maize silage and crushed grain. The digester chamber load is adjusted to normal (3.5-4.5 g ods/l/d) to high values (9-12 g ods/l/d) during the series of tests. Additives are added based on pH value, i.e. the additives are added if the pH value in the fermenter falls below a minimum of 6.3. The additives are added such that the pH value is adjusted to 7.5.

The following parameters are measured on a continuous basis:
- quantity of gas
- quality of gas
- pH value
- buffer capacity
- fatty acid pattern 2.1 Continuous Test Series (1)

In continuous test series (1), the additives are added repeatedly as soon as acidification is imminent. A constant excessive digester chamber load is preset.

Figure 6:
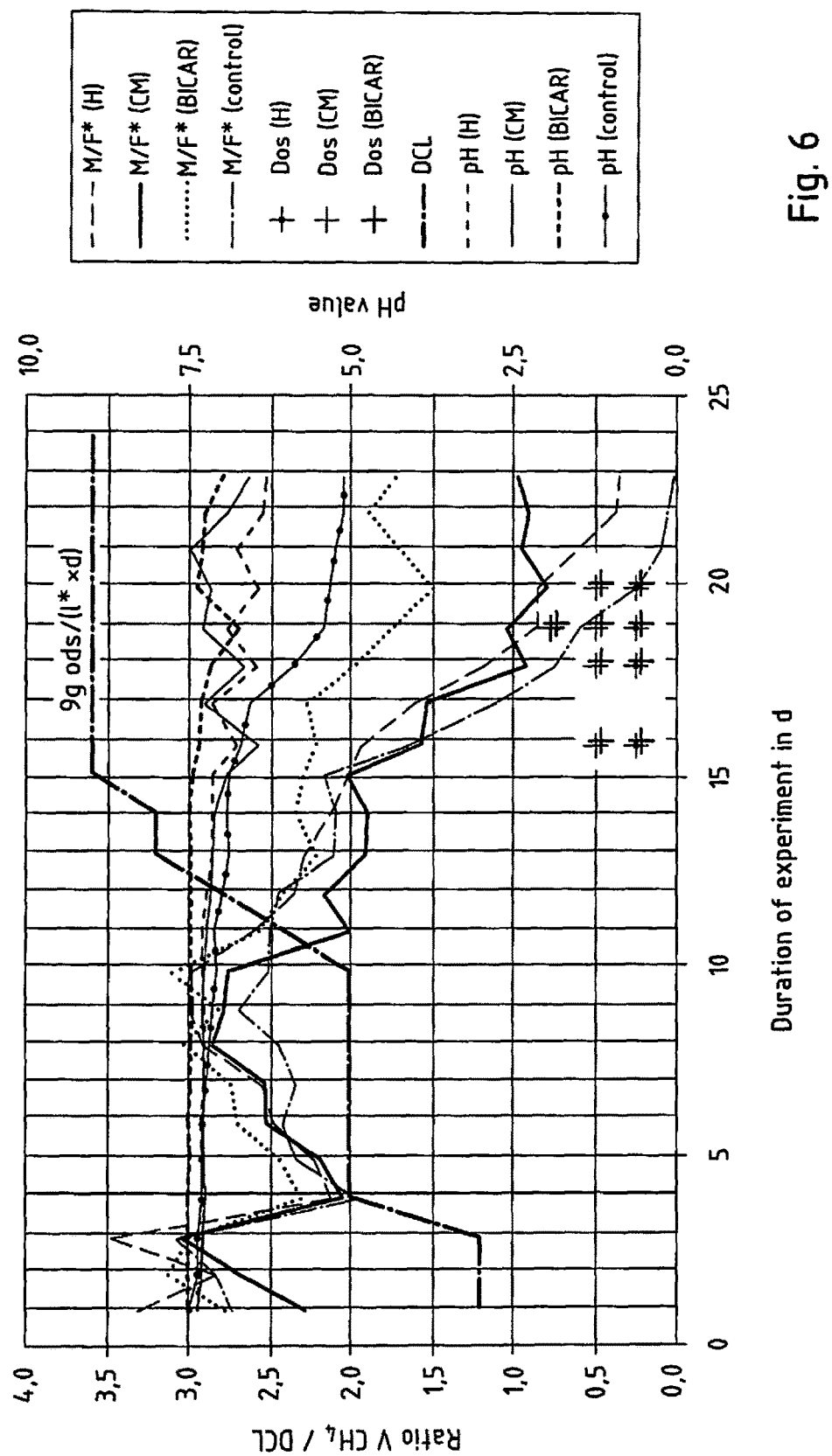
FIG. 6 shows the ratio of methane gas volume to digester chamber load in a continuous fermentation test, where the digester chamber load remains consistently high following hyperacidification.

As shown in FIG. 6, without the addition of the additive, the fermentation process comes to a complete standstill upon overfeeding and the resulting hyperacidification (see control sample). However, the repeated addition of additives as soon as the pH value clearly starts to fall and the buffer capacity decreases can stabilise the process permanently. The varying effectiveness of the additives can be seen from the course of the curve M/F (=ratio of methane gas volume to digester chamber load). Said curve shows that Biocal CM produces the best results among the lime-based products.

2.2 Continuous Test Series (2)

Figure 7:
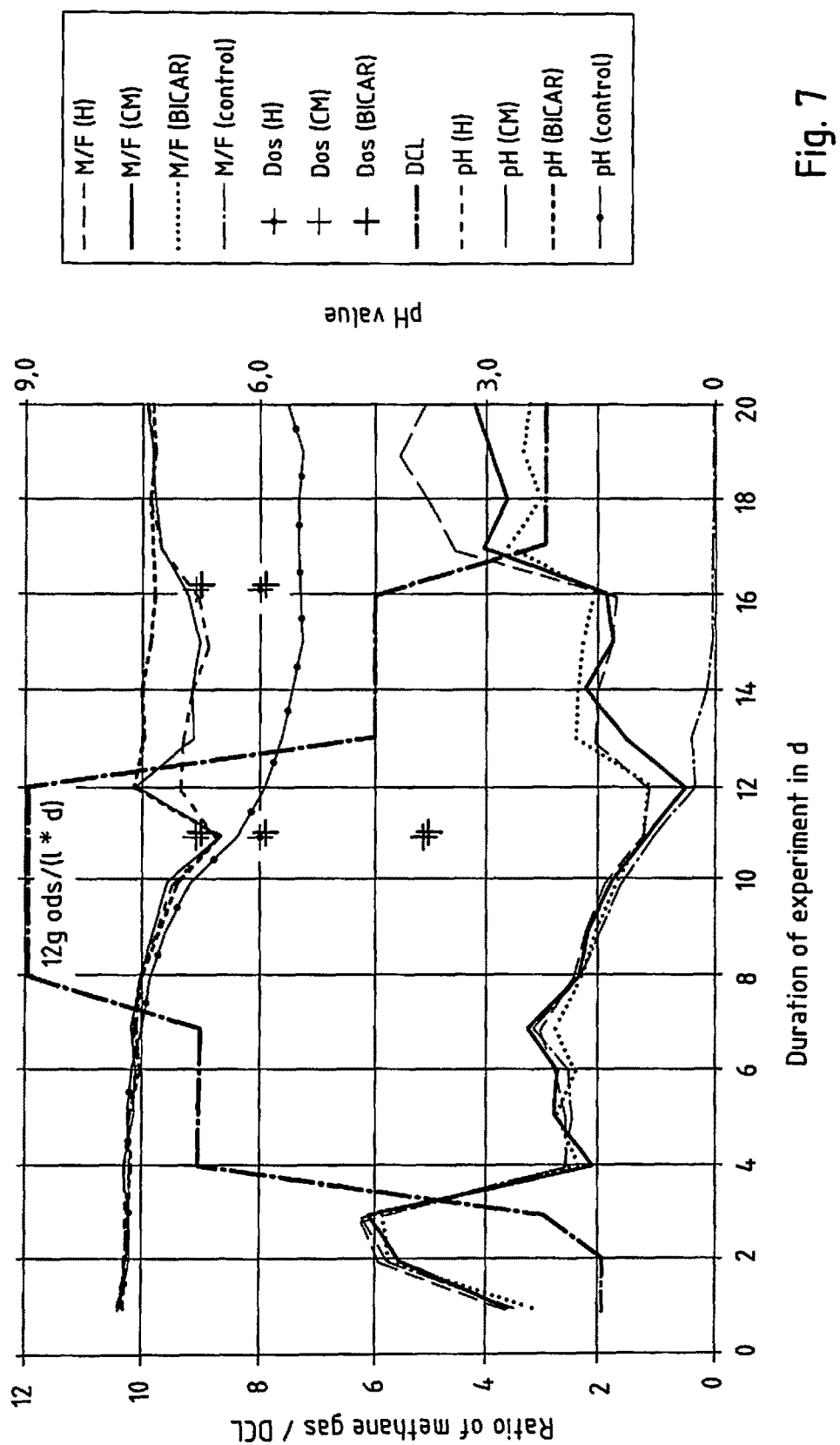
FIG. 7 shows the ratio of methane gas volume to digester chamber load in a continuous fermentation test where the digester chamber load is reduced following hyperacidification.

FIG. 7 shows continuous test series (2). The process is stabilised in this case by adding additives twice as soon as the pH value clearly starts to fall and the buffer capacity decreases where the digester chamber load is reduced in parallel in two stages.

It is evident from FIG. 7 that without additive addition and in the event of continued overfeeding and the resulting hyperacidification, the fermentation process comes to a complete standstill. This result corresponds to the result achieved in continuous test series (1).

It shows that in this series of tests, Biocal H has the best results, followed by Biocal CM.

2.3 Continuous Test Series (3)

Figure 8:
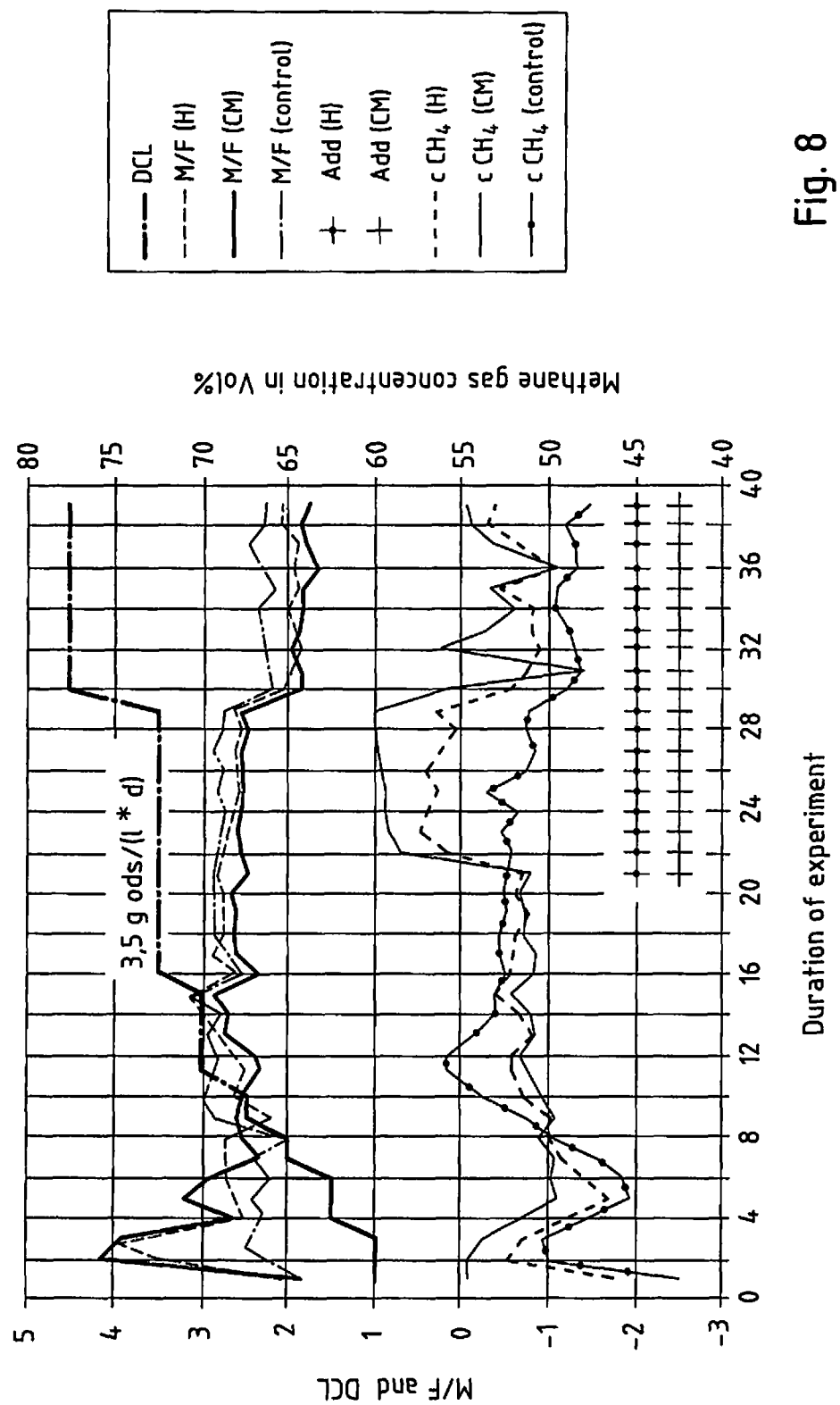
FIG. 8 shows the ratio of methane gas volume to digester chamber load in a continuous fermentation test where the digester chamber load is normal.
Figure 9:
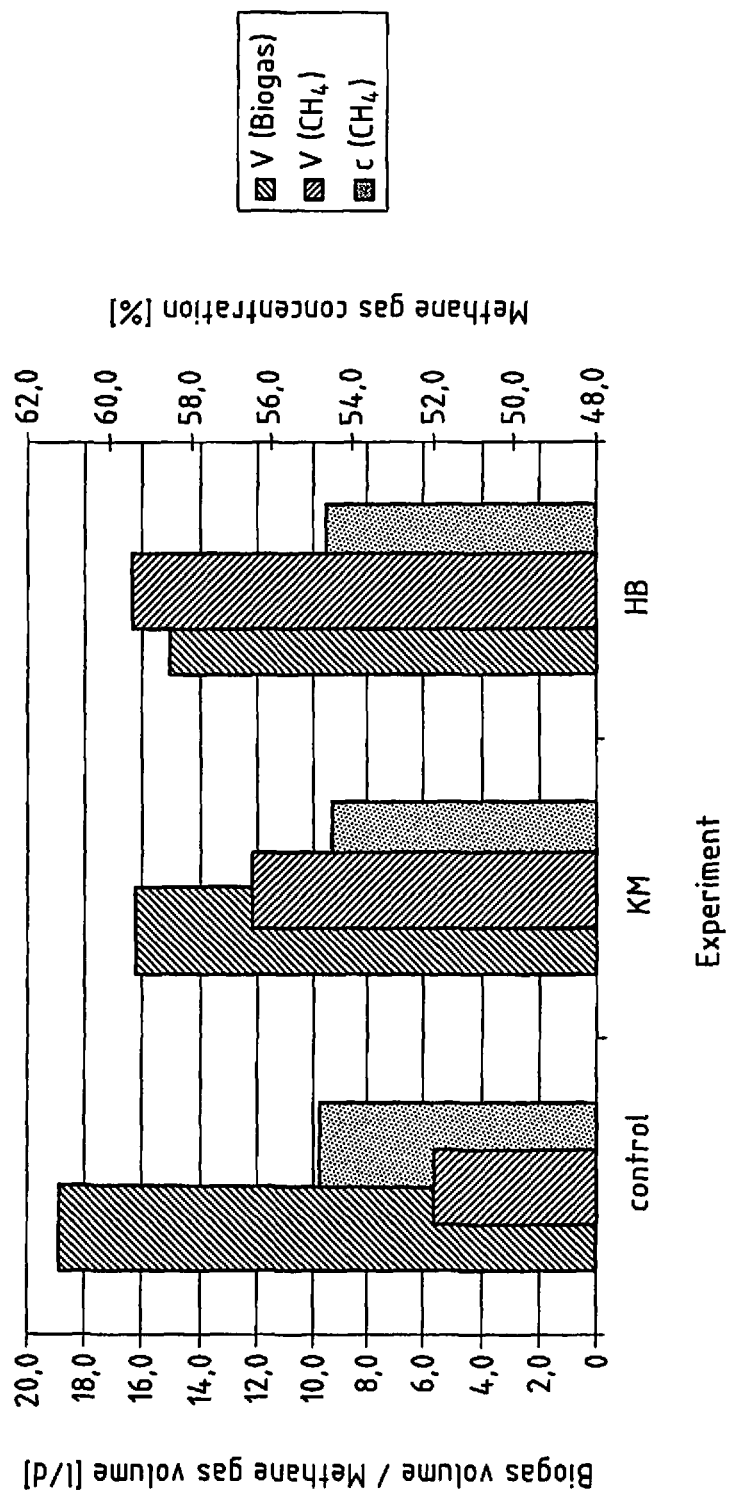
FIG. 9 shows the concentration of methane gas in a continuous fermentation test where the digester chamber load is normal.

FIG. 8 and FIG. 9 show continuous test series (3). In this series of tests, the additives are added during normal operation and when the digester chamber load is normal.

It is evident from FIG. 8 and FIG. 9 that a significantly higher concentration of methane gas can be achieved by adding the additives. This effect is particularly clear when using Biocal H and, in particular, Biocal CM. The reduction of the concentration of $CO_2$ in the biogas is stoichiometrically equivalent to the quantity of additives added.

$\Delta V\ CO_2$=0.011 mol/l at 0.01 mol/l metered quantity of Biocal H $\Delta V\ CO_2$=0.015 mol/l at 0.01 mol/l metered quantity of Biocal CM.

2.4 Continuous Test Series—Fatty Acid Pattern

Figure 10:
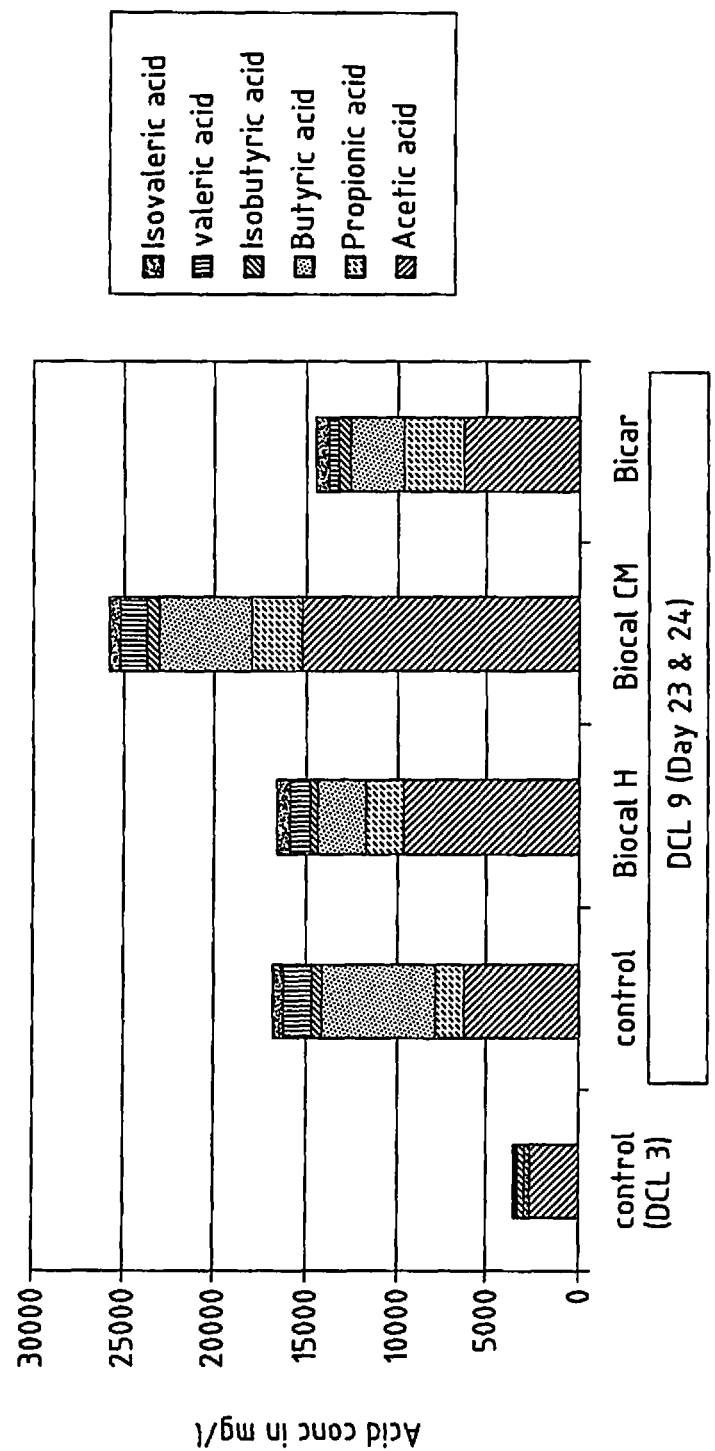
FIG. 10 shows the fatty acid pattern of a substrate in a continuous fermentation test where the digester chamber load is normal and FIG. 11 shows the neutralisation kinetics of the additives used.

FIG. 10 shows how the fatty acid pattern of the organic materials used in the tests changes in the continuous test series. The change at high and normal digester chamber load is analysed.

When the digester chamber load is high, overfeeding creates an accumulation of fatty acids. This is an indicator of the inhibition of decomposition during the fermentation process. Moreover, it is evident from FIG. 10 that the fatty acid patterns achieved vary depending on the respective additive used. The highest overall acid concentration (factor 7) and acetic acid concentration (factor 6) compared with the initial situation was achieved with Biocal CM. The acetic acid/propanoic acid ratio halves when using Biocal H and Biocal CM compared with the initial situation (ratio=9).

When the digester chamber load is normal, the total fatty acid concentration is increased compared with the control sample during stable operation by using Biocal H or Biocal CM. The fatty acid patterns differ from the control sample.

2.5 Continuous Test Series—Neutralisation Kinetics

Figure 11:
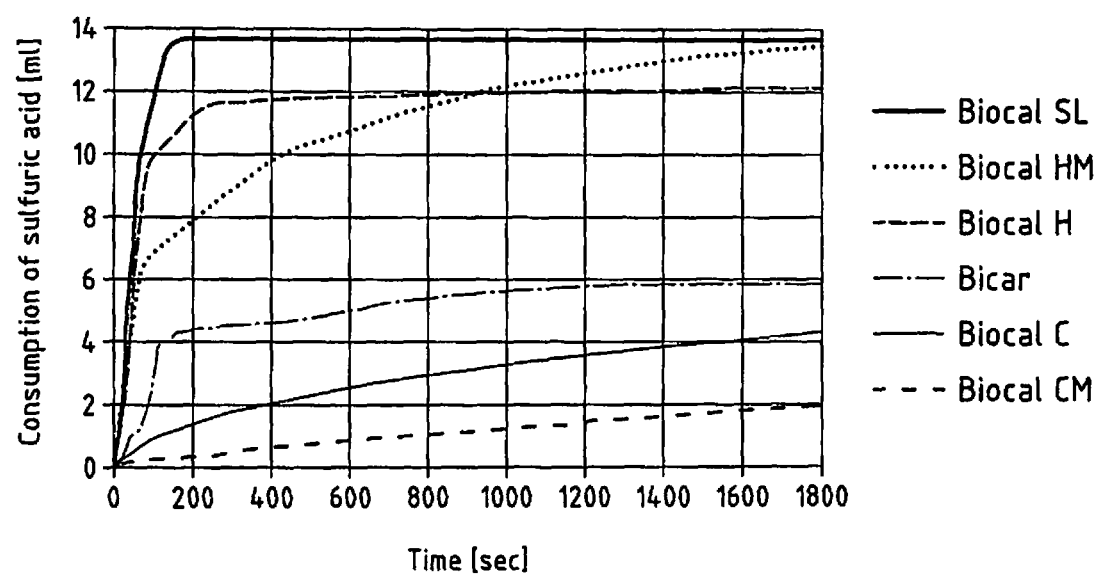

FIG. 11 shows the neutralisation kinetics of the various additives under analysis. The range of product-specific reaction kinetics is determined by titration with sulphuric acid to a pH value of 6. It is evident from FIG. 11 that Biocal H reacts very spontaneously. Biocal CM, on the other hand, has a delayed reaction.

2.6 Summary Assessment

In summary, it was possible to demonstrate that the purposeful addition of fine-particle, lime-based materials can achieve fast process regeneration in the event of substrate acidification. This is particularly useful in the case of impact loads, for example, as a result of the increased use of agricultural waste. It was established in particular that fine-particle, lime-based materials have no tendency or only a slight tendency to settle in the fermenter. Thus, the pH value can be stabilised reliably during fermentation in the process according to the invention. This enables the use of high energy substrates at a simultaneously high volumetric loading.

In the case of permanent use, the lime-based materials employed have the advantage of increasing the buffer capacity in the bioreactor. Consequently, they act preventatively against acidification.

Moreover, it was established that the addition of these materials leads to an increase or a change in the fatty acids in the substrate.

A further surprising advantage of using fine-particle, lime-based materials consists in increasing the concentration of methane gas in the biogas. According to current technical knowledge, the increase in the concentration of methane gas takes place as a result of in-situ precipitation of carbon dioxide ($CO_2$). A high concentration of methane gas is particularly advantageous when processing biogas for direct feeding into the natural gas supply. Moreover, the efficiency in terms of energy recovery in combined heating and power stations is increased.

When used both permanently and sporadically, the lime-based materials are characterised by a hygienically purifying effect. This is particularly advantageous when using agricultural waste as a substrate. In addition, digestate is enriched by nutrients, which originate from lime-based materials, which can be beneficial when using digestate as an organic fertiliser. In respect of plant nutrition, calcium and magnesium in particular are relevant in this context.

The invention claimed is:

1. A process for production of biogas from a biodegradable substrate under substantially anaerobic conditions, comprising the following steps:
   introduction of said biodegradable substrate into a reaction space,
   addition of a lime-based material to said biodegradable substrate, biodegradation of said biodegradable substrate to form biogas, wherein said lime-based material is added as fine particles with a particle diameter $d_{97}$ of 1 to 70 µm and a particle diameter $d_{50}$ of 1 to 8 µm, and wherein said lime based material is added as a preventative measure irrespective of the pH value of said substrate to increase the buffer capacity of said substrate to prevent acidification.

2. The process of claim 1, wherein said lime-based material is selected from the group consisting of hydrated lime, lime milk, lime stone powder, burnt lime, dolomite stone powder, semi-burnt dolomite, dolomite hydrate, semi-hydrated dolomite and/or sodium hydrogen carbonate.

3. The process of claim 1, wherein the particle diameter $d_{97}$ of said lime-based material is from 1 to 50 µm.

4. The process of claim 1, wherein said lime-based material is then added when the pH value of said biodegradable substrate falls below 7.5.

5. The process of claim 1, wherein said lime-based material is added in such a quantity that the pH value of said biodegradable substrate is adjusted to from 6.3 to 7.8.

6. The process of claim 1, wherein said lime-based material is added at a quantity of from 0.0001 to 0.05 mol/l based respectively on the volume of said reaction space.

7. The process of claim 1, wherein said lime-based material is added in such a quantity that the buffer capacity, expressed as $CaCO_3$ concentration per litre of said volume of said reaction space, is adjusted to a value greater than 10 g/l.

8. The process of claim 7, wherein said step of formation of biogas is caused by methanogenic bacteria.

9. The process of claim 7, wherein at least two stages of said biodegradation step take place in said reaction space.

10. The process of claim 1, wherein said biodegradation step comprises the following steps:

splitting of carbohydrates, fats and/or proteins in said biodegradable substrate into cleavage products comprising sugar, fatty acids, amino acids and/or bases, fermentation of said cleavage products into fermentation products comprising carboxylic acid, gases and/or alcohols, formation of methanogenic substrates comprising acetic acid, hydrogen and/or carbon dioxide, formation of biogas comprising methane and carbon dioxide.

11. The process of claim 10, wherein said step of splitting of the carbohydrates, fats and/or proteins in the substrate is caused by hydrolytic bacteria.

12. The process of claim 10, wherein said step of fermentation of the cleavage products into fermentation products is caused by fermentative bacteria.

13. The process of claim 10, wherein said step of formation of methanogenic substrates is caused by acetogenic bacteria.

14. The process of claim 1, wherein said biodegradable substrate has a carbon:nitrogen:phosphorous:sulfur or C:N:P:S ratio of approx. 600:15:5:1.

15. The process of claim 1, wherein said biodegradable substrate has a carbon:nitrogen or C:N ratio of from 10 to 30.

16. The process of claim 1, wherein the reaction temperature in said reaction space is adjusted to from 28° C. to 46° C.

17. The process of claim 1, wherein a volumetric loading, measured as the mass of organic dry substance of the substrates used added per unit of fermenter volume and time, of from 0.5 to 5 kg ods/$m^3$ per day is set.

18. The process of claim 1, wherein the particle diameter $d_{97}$ of said lime-based material is from 6 to 30 µm.

19. The process of claim 1, wherein the particle diameter $d_{97}$ of said lime-based material is from 4 to 15 µm.

20. The process of claim 1, wherein said lime-based material is added at a quantity of from 0.001 to 0.02 mol/l, based respectively on the volume of said reaction space.

21. The process of claim 1, wherein said lime-based material is added at a quantity of from 0.005 to 0.01 mol/l, based respectively on the volume of said reaction space.

22. The process of claim 1, wherein said lime-based material is added in such a quantity that the buffer capacity, expressed as $CaCO_3$ concentration per litre of said volume of said reaction space, is adjusted to a value greater than 15 g/l.

23. The process of claim 1, wherein said lime-based material is added in such a quantity that the buffer capacity, expressed as $CaCO_3$ concentration per litre of said volume of said reaction space, is adjusted to a value selected from 15 g/l, 16 g/l, 17 g/l, 18 g/l, 19 g/l or 20 g/l.

24. The process of claim 1, wherein a volumetric loading measured as the mass of organic dry substance of the substrates used added per unit of fermenter volume and time, of from 1 to 3 kg ods/$m^3$ per day is set.

* * * * *